United States Patent [19]

Wengong et al.

[11] Patent Number: 4,816,594

[45] Date of Patent: Mar. 28, 1989

[54] COUPLING AGENT SYSTEM OF ALUMINIUM

[75] Inventors: Zhang Wengong; Chen Wending; Chen Tianan, all of Fuzhou, China

[73] Assignee: Fujian Teachers University, Fuzhou, China

[21] Appl. No.: 851,144

[22] Filed: Apr. 11, 1986

[30] Foreign Application Priority Data

Apr. 12, 1985 [CN] China ................................. 85102942

[51] Int. Cl.$^4$ ................................................ C07F 5/06
[52] U.S. Cl. ..................... 556/182; 556/183; 556/174; 556/176; 556/177; 556/188; 260/414
[58] Field of Search ............... 556/182, 183, 174, 176, 556/177, 188; 260/414

[56] References Cited

U.S. PATENT DOCUMENTS

| | | | |
|---|---|---|---|
| 3,042,696 | 7/1962 | Aldridge | 260/448 |
| 3,070,616 | 12/1962 | Flanagan | 260/448 |
| 3,127,432 | 3/1964 | Johnson | 260/448 |
| 3,538,136 | 11/1970 | Schmidt | 260/448 |
| 3,736,342 | 5/1973 | Ichiki et al. | 260/448 AD |
| 3,856,841 | 12/1974 | Merkl | 556/182 X |
| 3,905,936 | 9/1975 | Hawthorne | 260/40 R |
| 3,969,387 | 7/1976 | Merkl | 556/182 |
| 3,988,333 | 10/1976 | Suzuki et al. | 556/182 UX |
| 4,075,178 | 2/1978 | Turner | 260/75 T |
| 4,132,724 | 1/1979 | Turner | 260/448 AD |
| 4,272,448 | 6/1981 | Bernard et al. | 260/448 R |
| 4,283,316 | 8/1981 | Bonsignore | 260/234 A |
| 4,514,555 | 4/1985 | Taniguchi et al. | 528/9 |
| 4,525,307 | 6/1985 | Pratt | 556/182 |
| 4,529,555 | 7/1985 | Matsushita | 556/174 |

FOREIGN PATENT DOCUMENTS

| | | | |
|---|---|---|---|
| 54-20055 | 2/1972 | Japan | 556/182 UX |
| 56-125475 | 10/1981 | Japan | 556/182 UX |
| 57-96030 | 6/1982 | Japan | 556/182 UX |
| 57-195163 | 11/1982 | Japan | 556/182 UX |
| 57-205431 | 12/1982 | Japan | 556/182 UX |
| 57-200438 | 12/1982 | Japan | 556/182 UX |
| 60-36573 | 2/1985 | Japan | 556/182 UX |

*Primary Examiner*—Paul F. Shaver
*Attorney, Agent, or Firm*—Ladas & Parry

[57] ABSTRACT

The present invention relates to aluminate coupling agents, their synthesis and applications. Metallic aluminum is reacted with lower alcohols, then reacted with selected longer chain alcohols, phenols, carboxylic acids etc., satisfied the coordination number of aluminum to give aluminate coupling agents having good hydrolytic stability and lower associativity. They can be used directly as typical coupling agents in processing of composition products such as plastics, rubber, coatings and laminates etc., and as adhesive promoter or primer to treat fillers, pigments and various materials in order to improve the processing and the quality of products, to increase the dosage of filler, to develop new products, to reduce energy consuming and cost of products.

18 Claims, No Drawings

COUPLING AGENT SYSTEM OF ALUMINIUM

TECHNICAL FIELD

The present invention relates to aluminate coupling agents, their syntheses and applications.

Coupling agent is also called adhesive promoter or surface primer. Typical coupling agent is a kind of chemical materials or products which contains at least two chemical radicals in tis molecule and can react with two different phases of materials in certain mixed or adherent systems to combine the two phases tightly together physically or physicochemically.

Over last thirty years, coupling agents were used widely for plastics, rubber, coating, adhesives, toughened glassfibre reinforced plastics, laminates, printing ink, shoe polish, electric products, textile fabric and surface modification for various materials and so on. In these respects, coupling agents and their application have played a role in the improvement of quality, development of products, improvement of process properties, reduction of energy consume and cost, and provided a new route for their applications. Therefore, coupling agents become all the more a kind of important products and auxiliaries in fine chemical industry.

DESCRIPTION OF THE PRIOR ART

In the fifties of this century, chromium systems coupling agent represent by "Volan" series have been created (U.S. Pat. No. 352,740). Afterwards, volan has not been significantly developed due to the toxicity of cromium ion and enviroment pollution caused by it almost at the same time, created silicon system coupling agent represented by aminosilane (J. G. Masdenet et. al., "Adherends and Bonding technology" Section C, p. 462–652). In the seventies of this century, kenrich Petrochemical of U.S.A. had synthesized succesfully titanium coupling agent represented by TTS (S. J. Monte et. al. 32nd Annual Technical Conference. Section 4-E, 1977, p. 1–29). In 1983, Cavedon Chemical of U.S.A. recommended zircoaluminate system coupling agent represented by seven of zircoaluminate (L. B. Cohen, Plastics Engineering, 1983.39 (11), 29–32).

Other organic compounds and organo-metallic compounds containing other metallic atoms are also used as coupling agent, but their properties and importance can not be compared favorably with four coupling agent systems above mentioned.

Furthermore, in recent years, chelate compounds of organic cluminium have been put forth for using as drier of coatings (B.P.1462610), surface treating agent of glassfibre of reinforced epoxy resin (J.P.83.79023), adhesive promoter of coating layer to glass (C.A.99.214185g), fibreglass surface threating agent in copolymer of acryl ester-methacrylic ester (C.A.97.56624b); and to improve the addhesive property of intergrated circuit to polyacetylimide instead of aminosilane coupling agent (J. Electrochemical Soc. 1982. 2278–2282). Aluminates were not yet considered to be used as coupling agent till 1983 because they are unstable and easy to hydrolyze L. B. Cohen, plastic Engineering, 1983, 11, 29)

In a word, investigation production and application are still concentrated on silica and titanium, the most important systems in coupling agent. But up to now these two systems of coupling agent are made by using their coresponding anhydrous chlorides as starting materials Thus, the preparation of these coupling agent bring about more expensive production cost, more serious corrosion and more complicated process, resulting in high price products and limited applications.

SUMMARY OF THE INVENTION

The object of the present invention is to provide a new coupling agent system, which is of easy to synthesize, low production cost and good quality.

In the present invention, we selected aluminium, which is rich in resource and cheap in price, as the central atom of coupling agent, and took advantage of its active and amphotric characteristics to react directly with lower alcohols to form the intermediate of trialkoxyl aluminium which can be treated with the substances defined chain length, proper steric hindrance and acidic radicals such as hydroxyl, phenolic group, carboxyl, phosphyl, sulfonyl, etc. and other functional group, and esters thereof; ethers as well as anhydrides. The final products aluminate or derivatives thereof prepared in such manner have proper stability against hydrolysis. At the same time, we use proper method of satisfying coordination number of aluminium 1–3 in order and to overcome or decrease the associativity of aluminate and derivatives thereof. The aluminate or derivative thereof thus obtained possess necessary chemical and physical properties for coupling agent.

Based on the teaching of present invention, the new coupling agent system of aluminium in accordance with the invention possesses the following basic structure:

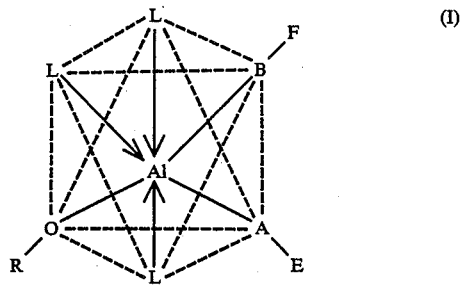

(I)

Wherein Al is aluinium, the central atom of coupling agent; R is straight chain, branched chain or cyclic alkyl or aryl with 1–6 carbon atoms; O is oxygen atom, therefore, R—O— may be methoxy, ethoxy, n-propoxy, iso-propoxy, n-butoxy, iso-bytoxy, tert-butoxy, various isomeric amyloxy, various isomeric hexoxy and phenoxy etc; L is the same, different or mixed organic or inorganic ligands containing atoms with isolated electron pair such as ketones, aldehydes, amines, alcohols, ethers, esters heterocyclic compounds. A—E and B—F are the same, different or mixed longer chain radicals (straight, branched or cyclic) having two different functional groups; A and B may be the same or different atoms or atomic groups which combined directly to aluminium atom by covalent bond, such as oxygen or various acyloxy etc; E and F are the same, or different long-chain radicals (straight, branched or cyclic) which contain 6–20 or more carbon atoms, preferably 12–22, and possess proper steric hindrance and other functional group, which can react with polymerchain chemically, physicochemically or by physically. Therefore long chain A—E and B—F may be straight, branched or cyclic long chain radicals containing 6–20 or more carbon atoms, preferably 12–22, possesing proper steric hindrince and other functional above mentioned gorups such as alkyl (aryl) oxy, alkyl (aryl) acyloxy, various alkyl phosphate radicals, various alkyl sulfonyloxy radicals monohydroxyl and monoacyloxy of esters and their substituted derivatives.

It is necessary to point out that besides having aluminium atoms as central atoms, the new coupling agent system of aluminum with above-mentioned basic structure, also have the following characteristics:

(1) In long chains E—A or F—B—, if steric hindrance of E or F is large enough or the distance from E to A or from F to B is 3-4 atoms, within which atoms with isolated electron pair exsist, L may be omitted. Therefore, the number of radicals directly connected to the central atom of aluminium in coupling agent of this invention is 3-6, generally, 4-5, three of them are combined by covalent bonding and the rest by coordination links.

(2) The hydrolytic stability of products can be controlled by chain length and steric hinderance from E—A and F—B structure.

(3) Associativity of final products can be overcome or reduced by choosing L structural type, size and number and coordinated with (2).

(4) The hydrolytic reactivity of products can be adjusted by choosing the structure, number of carbon atom and steric hingrance of R—O—.

(5) Low-polyalkyloxy aluminium having polymeriztion degree of 2-4 can be obtained by appropriately controlling hydrolytic condensation of trialkyloxy aluminium. The resulting product can be converted into the new coupling agent system of aluminium through synthesis. The possible structure is shown in formula (II):

In formula (II), B' is the residual part of formula (I), in which oxygen atom in B be omitted.

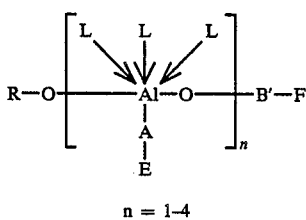

n = 1-4

Obviously, the coupling agent system of aluminium according to the present invention is not only essentially different in structure from those known coupling agent systems of titanium silica, chromium as well as zirconium-aluminium and the other organic compounds used as coupling agent, but also evidently distinguished from the old aluminates used as surface modifier of filler and figment (U.S. Pat. No. 3,905,936).

Process and procedure for synthesizing the coupling agent system of aluminium in accordance with the invention are:

(I) SYNTHESIS OF INTERMEDIATE

1. Aluminium trialkyloxide; To various shapes of metallic aluminium, was added 1-10 times by weight (theoretical amount) of lower alcohols (phenols) having 1-6 carbon atoms such as methanol, ethanol, n-propanol, iso-propanol, n-butanol, iso-butanol, tert-butanol, various isomeric amylalcohols, various isomeric hexanols and phenol etc, preferably iso-propanol and n-butanol, if desired, catalyst (0.01-1% by weight of Al metal) such as chlorides or acetates of copper, silver, mercury or their coordinative substances with reducing agents bromibe iodine etc can also be added. Reflux the mixture at 20°-160° C. For 2-8 hours, evaporize out excess lower alcohol under normal pressure, and then distil out the product aluminium trialkyloxide under reduced pressure. The reaction equation is as follows:

$$2AL + 6ROH \rightarrow 2AL(OR)_3 + 3H_2 \quad (III)$$

The yield of aluminium trialkyloxide is 45-100%, recovery of lower alcohol is 85-98%.

2. Lower-polyalkyloxy aluminium: Aluminium trialkyloxide or aluminium trialkyloxide dissolved in appropriate amount of inert solvent is heated and refluxed, while gradually introduce 0.001-8.8% of steam by weight of aluminiu trialkyloxide, continue refluxing for 1-4 hours, evaporize off sovlvent under normal pressure, and a small amount of acid, alkali or oxide, such as sulfuric acid, hydrochloric acid, phosphoric acid, sodium hydroxide, calcium hydroxide, calcium oxide or magnesium oxide is added as condensation catalyst; Then the mixture obtained is heated and reluxed under reduced prre gradually raise the temperature up to 160°-200° C. The reaion carried out for 2-4 hours. Distil out lower-polyalkyloxyl aluminium optionally. The reaction equations are:

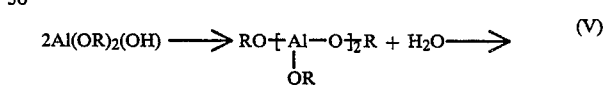

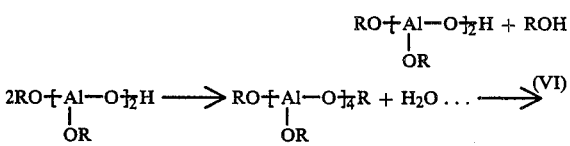

The yield of lower-polyalkyloxyl aluminium is 10-95%.

(II) EXCHANGE REACTION

To 1 gram-molecule of trialkyoxyl aluminium or lowpolymerized aluminate or theri mixtures, was added (n+1) mole of F—B—H [or E—A—H or their mixture], if desired appropriate amount of inert solvent is added, the mixture is refluxed at 40°-250° C. for 0.5-4 hours, distil out low boiling product and solvent. The reaction equations are:

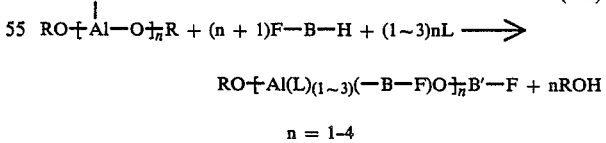

n = 1-4

The yield of aluminate or lower-polyaluminate is 90-100%. F—B—H or E—A—H used in the present invention can be:

1. Alkoxy series: Various alcohols and their substituted derivatives such as octanol, nonanol, decanol, lauranol, myristyl alcohol, palmitinyl alcohol, stearyl alcohol, oleinyl alcohol, linolenyl alcohol, linolyl alcohol and their iscomers or mixtures; and methanol, terpenol, terpineol, geraniol, linalool, nerol ect. and dodecylphenyl methanol, m-methoxyl phenyl methahol and furfuryl alcohol etc.

2. Phenoxyl series: Various phenols and their substituted derivatives, such as dodecyl phenol, didodecyl phenol tridodecyl phenol, dodecyl cresylol 2.5-dimethyl-4-dodecyl phenol, tetradecyl phenol, ditetradecyl phenol, tritetradecyl phenol, 3-pentadecadienyl phenol, 3-(pentadecadiene)-5-hydroxyphenol, cetylphenol, dicetyl phenol, p-isopropylphenol ect.

3. Carboxyl series: Various carboxylic acids and their substituted derivatives such as octanoic acid, nonanoic acid, decanoic acid, lauric acid, myris-tic acid, palmic acid, stearic acid, iso-stearic acid, oleic scid, linoleic acid, linolenic acid, castoic acid cycloalkanoic acid, tall oil, and resinic acids, alkyl benzoic acids etc.

4. Alkyl phosphoryl series: Various alkyl phosphates such as diisoockyl phosphate, di-isooctyl phosphite, diisooctyl pyrophosphate, diisooctyl pyrophosphite etc.

5. Alkyl sulfonyl series: Various alkylsulfonic acids benzene sulfonic acids and their substituted derivatives, such as dodecyl, sulfonic acid dodecyl phenyl sulfonic acid, didodecyl phenyl sulfonic acid tridodecyl phenyl sulfonic acid, tetradecyl sulfonic acid, tetradecyl phenyl sulfonic acid, di-or-tri-tetradecyl phenylsulfonate, cetyl sulfonic acid, cetylphenyl sulfonic acid ect.

6. Alkyl thiosulfuryl series: Various alkyl sulfates, such as dodecyl sulfate, dodecyl sulfite, tetradecylsulfate, cetyl sulfate and cetyl phenyl sulfate etc.

7. Monohydroxyl or mono-carboxyl esters series: such as monobuty (or monooctyl) phthalate, phthalic anhydride, maleic anhydride, glycerol dialiphatic carboxylate, propanediol monocarboxylate and lowerpolyglycol monocarboxylate.

8. Mixtures of two or more F—B—H or E—A—H in above-mentioned series.

According to above description, Aluminium being the central atom of the new coupling agent in accordance with the invention is an essential difference invention when compared with the known coupling agent systems of chromium, silica titanium and zirconium aluminium and other coupling agent system, therefore, systhesis (preparation or production) of the new coupling agent system of aluminium in accordance with the invention has the following advantages:

1. Metallic aluminium is the starting material, which is rich in resources and low in price. The intermediate trialkyloxyl aluminium can be obtained by one-step reaction, then by hydrolytic condensation to obtain lower-polyabyloxyl aluminium.

2. The synthetic reaction of intermediate, trialkyloxy aluminium or its lower condensed polymer can ben carried out rapidly with simple technology and high yield, it is non-corrosive, and can greatly reduce production cost.

3. Owing to above two points, cost of final product is lower than the other systems of coupling agent.

4. The stability against hydrolysis and small associativity of aluminate, its lower condensed polymer and its mixtures, have been brought about by using longer chain having 6-20 or more carbon atoms and defined steric hindrance as side radical which also contains other functional groups reacting chemically, physicochemically or physical wringing with polymer molecular chain controlling the degree of condensation and satisfying coordination number 1-3 of central atom of aluminium.

Furthermore, the new coupling agent system of aluminium in accordance with the invention is non-toxic, light color in comparison with titanate coupling agent. The new coupling agent of aluminium varies in series, species and properties to meet different requirements and applications. New coupling agent system of aluminium in accordance with the invention can be applied to two aspects:

(I) as typical coupling agent used in polycomposition products containing organic and inorganic compounds such as plastics, rubber, coating, adhersive, glass fiber reinforced plastics, laminates, printing ink and shoe polish etc. There are two basic method of use:

1. Pretreatment method: Filling materials with water content less than 0.5% such as light calicium carbonate, heavy calcium carbonate, aluminium trihydroxide, silica dioxide, titanium dioxide, zinc oxide, barrium sulfate gypsium powder, lithopone etc., or pigments such as titanium white powder, carbon black, iron oxide red, chromium yellow etc, and 0.1-3.5% of new coupling agent system of aluminium are mixed together in an appropriate equipment and stir at 30°-150° C. for 2-30 minutes. The modified filling materials or pigments are obtained.

2. Direct addition method: Add directly appropriate amount of new coupling agent system of aluminum to products containing organic and inorganic compounds in the process of production.

The new coupling agent system of aluminium used in above objects decrease the viscosity of system, improve processing, reduce energy consuming and, production cost, improve quality and increase the dosage of filler, or increase the viscosity of system for preventing settlement and flowing Hanging etc.

(II). As adhesive promoter or surface primer to treat surfaces of materials, such as filler, pigment, reinforcing material, plastics, metal, carrier of charomategraphy, rock, cement, glass, wood and bamboo, textile and electric products, in order to improve properties of surface or promote adhesion with other materials by spray coating, brush cooting and impregnating after diluting with suitable solvent.

Examples of the New coupling agent system of aluminum and their syntheses and applications in this invention are shown below:

EXAMPLE 1

360 g anhydrous isopropanol, 0.0959 g mercuric salt and 13.5 g metallic aluminium scraps was refluxed at 83°-90° C. for 2-8 hours, evaporated off excess isoproprand under normal pressure, triisopropoxyl aluminum was obtained by collecting distillation fraction of 110°-200° C. under reduced pressure of 1-10 mmHg. yield 90-100%.

To 20.4 g triisopropoxyl aluminum, 57.9 toluenee and 4.5 g dodecylamine was added 54.0 g octodecyl alcohol, and refluxed at 83°-120° C. for 0.5-1 hr., evaporated off solvent and isopropanol under normal pressure, Isopropoxyldiocta-decyoxyl dodecylaminoaluminum was obtained, yield 95-100%.

EXAMPLE 2

To 20.4 g triisopropoxyl aluminum, 50.3 benzene and 14.6 g cetylamine was added dropwise 56.5 g oleic acid with strirring then refluxed at 78°-90° C. for 0.5-1 hr., evaporated off benzene and isopropanol under normal pressure. Isopro-poxyldioleioxycetylaminoaluminum was obtained, yield 96-100%.

EXAMPLE 3

To 20.4 triisopropoxylalumium and 30.4 g glycoldiester was added dropwise 64.6 g disooctyl phosphate, refluxed at 83°–130° C. for 0.5–1 hr., evaporated off isopropanol under normal pressure, a mixture of aluminates was obtained, yield 98–100%.

EXAMPLE 4

To 20.4 g triisopropoxyl aluminum and 23.0 g DOP was added gradually 27.2 g p-isopropylphenol with stirring, refluxed at 83°–200° C. for 0.5–1 hr., evaporated off isopropanol under normal pressure, a mixture of aluminates was obtained, yield 94–100%.

EXAMPLE 5

To 20.4 g triisopropoxylaluminum and 64.4 g DOP was added gradually 68.0 g dodecylmethylphenyl sulfite with stirrifng, refluxed at 83°–130° C. for 9.5–1 hr., evaporated off isopropanol under normal pressure, a mixture of aluminates was obtained, yield 93–100.

EXAMPLE 6

To 20.4 g triisopropoxylaluminum and 40.0 g xylene was added gradually 19,6 g butanedioic anhydride with stirring, refluxed at 83°–130° C. for 0.5–1 hr., evaporated off xylene under normal pressure, isopropoxyl di(monoisopropyl ester butanedioyl) aluminum was obtained, yield 97–100%.

EXAMPLE 7

To 20.4 g triisopoxylaluminum and 119.8 g DBP was added dropwise 123.3 g glyceryl dilinolenate with stirring, refluxed at 78°–200° C. for 0.5–1 hr., evaporated off isopropanol, a mixture of aluminates was obtained, yield 96–100%.

EXAMPLE 8

To 20.4 g triisopropoxylaluminum and 51.6 g DBP were added dropwise 28.3 g oleic acid and 27.0 g octadecyl alcohol with stirring, refluxed at 83°–200° C. for 0.5–1 hr., evaporated off isopropanol, a mixture of aluminates was obrtained, yield 90–100%.

EXAMPLE 9

To 100 parts of light calcium carbonate (water content 0.5%) was added 0.8 part of aluminate coupling agent Dl-429 in a high-speed mixer, stirred at 30°–150° C. for 10 minutes. Active-modified light calcium carbonate was obtained.

EXAMPLE 10

To 100 parts of heavy calcium carbonate was added 0.8 part of aluminum coupling agent Dl-429 in a high-speed mixer, stirred at 30°–150° C. for 10 minutes. Actixe-modified heavy calcium carbonate was obtained.

EXAMPLE 11

The viscosity of mixture of 50 parts of zinc oxide and 100 parts of paraffin oil was greater than $5 \times 10^4 CP$ (18° C.), it reduced to 440 CP. (18° C.) after adding 1% aluminate coupling agent Dl-429 (by weight of zinc oxide).

EXAMPLE 12

The viscosity of mixture of 50 parts of light calcium carbonate and 100 parts of paraffin oil was greater than $8.5 \times 10^4 CP$ (17.5° C.), it reduced to 690 CP (17.5° C.) after adding 1% aluminate coupling agent Dl-429 (by weight of calcium carbonate).

EXAMPLE 13

A PVA film was immersed into 5% solution of aluminate couplig agent Dl-429 in petroleum ether and refluxed at 60°–90° C. for 5 minutes. After washing the film several times with isopropanol, the surface of the film became hydrophobic from hydrophilic.

EXAMPLE 14

Modified light calcium carbonate obtained from example 9 was used for PVC foam slipper as filler. the dosage of the filler was increased from 20 phr. to 40–60 phs., process is easy and product is qualified or improved. (see table 1).

EXAMPLE 15

There is no influence on the processing and performance indices of produots when 40 parts of modified light calcium carbonate by aluminate coupling agent Dl-429 were used as filler for cross-linked foam PE sole, comparing with 10 parts of no modified light calcium carbonate was used as filler (ref. Table 2)

EXAMPLE 16

There is no difference on the processing and some performance indices exceeded the criteria when 30–50 parts of light calcium carbonate modified by aluminatc coupling agent Dl-429 were used as filler for PVC shoelace, comparing with 15 parts of no modified light calcium carbonate used as filler (ref. Table 3).

TABLE 1

Test results* of Products of PVC cellular foam Slippers Filled with light Calcium Carbonate Modified by New Aluminium Coupling Agent DL-429

| Test item | SG-77-7 standard | Value of test Sample | | | | | |
|---|---|---|---|---|---|---|---|
| | | 1# | 2# | 3# | 4# | 5# | 6# |
| | | Filler and dosage (phr) | | | | | |
| | | Calcium carbonate modified by DL-429 30 | Calcium Carbonate modified by DL-429 40 | Calcium Carbonate modified by DL-429 50 | Calcium Carbonate modified by DL-429 60 | Calcium carbonate modified by corresponding titanate 40 | unmodified Calcium Carbonate 30 |
| Tensile strength (kg/cm$^2$) | ≧24.0 | 30.6 | 30.9 | 28.3 | 27.6 | 27.1 | 20.4 |
| Elongation of break (%) | ≧130 | 162 | 164 | 161 | 153 | 156 | 145 |
| Shore hardness (Hs) | 25–35 | 26.0 | 28.0 | 27.0 | 27.5 | 24.0 | 19.5 |
| Specific gravity | 0.25–0.40 | 0.36 | 0.35 | 0.40 | 0.46 | 0.38 | 0.26 |

TABLE 1-continued

Test results* of Products of PVC cellular foam Slippers Filled
with light Calcium Carbonate Modified by New Aluminium Coupling Agent DL-429

| | | \#1 | \#2 | \#3 | \#4 | \#5 | \#6 |
|---|---|---|---|---|---|---|---|
| | | | | Value of test Sample | | | |
| | | | | Filler and dosage (phr) | | | |
| Test item | SG-77-7 standard | Calcium carbonate modified by DL-429 30 | Calcium Carbonate modified by DL-429 40 | Calcium Carbonate modified by DL-429 50 | Calcium Carbonate modified by DL-429 60 | Calcium carbonate modified by corresponding titanate 40 | unmodified Calcium Carbonate 30 |
| $(g/cm^3)$ | | | | | | | |

*Determined by Central Test Institute of Fujion

TABLE 2

Test results* of Products of Modified Cross-linked Foam PE Shoe sole Filled
with light Calcium Carbonate modified by New Aluminium Coupling Agent DL-429

| | | \#1 | \#2 | \#3 | \#4 | Contrast |
|---|---|---|---|---|---|---|
| | | | Value of test Sample | | | |
| | | | Filler and dosage (phr) | | | |
| test item | standard | Calcium Carbonate Modified by DL-429 10 | Calcium Carbonate Modified by DL-429 20 | Calcium Carbonate Modified by DL-429 30 | Calcium Carbonate Modified by DL-429 40 | unmodified Calcium Carbonate 40 |
| Tensile strength $(kg/cm^2)$ | ≧25 | 39.1 | 37.9 | 36.6 | 34.6 | Difficult to process |
| Elongation of break (%) | ≧150 | 301 | 275 | 275 | 253 | |
| Shore hardness (Hs) | 45 ± 5 | 60 | 65 | 64 | 64 | |
| Specific gravity $(g/cm^3)$ | 0.33-0.43 | 0.29 | 0.32 | 0.32 | 0.31 | |
| Bend crack (number of times) | ≧6 × 10$^4$ | Qualified | Qualified | Qualified | Qualified | Unqualified |

*Tested and determined by Fuzhou Plactic Rubber Factory

TABLE 3

Test results* of Products of PVC Shoelace Filled with
light Calcium Carbonate Modified by New Aluminium Coupling Agent DL-429

| | | \#1 | \#2 | \#3 | \#4 | \#5 |
|---|---|---|---|---|---|---|
| | | | | Value of test Sample | | |
| | | | | Filler and dosage (phr) | | |
| Test item | standard | Light Calcium carbonate 15 (phr) | light calcium carbonate modified by Coupling agent DL-429 30 (phr) | Light calcium carbonate modified by coupling agent DL-429 50 (phr) | Light calcium Carbonate modified by corresponding titanate coupling agent 30 (phr) | Light calcium carbonate modified by corresponding titanate coupling agent 50 (phr) |
| Tear strength of Crisscross angle of Lace (kg) | 10 | 38.0 | 31.1 | 24.0 | 36.0 | 28.3 |
| Draw strength of break of lace and (kg) | 12 | 21.0 | 19.4 | 15.4 | 17.1 | 16.8 |
| Shore hardness of lace (Hs) | 65-75 | 76 | 74 | 76 | 76 | 80 |

*Determined by Central Test Institute of Fujian

We claim:
1. The aluminate coupling agent comprising an aluminum atom as the central atom in the molecule, of the structure:

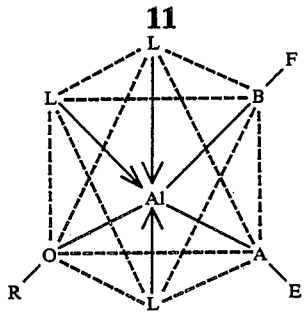

wherein Al is the aluminium atom, RO is alkoxyl or aryloxy containing 1-6 carbon atom: L are the same, different or mixed ligands having atoms with an isolated electron pair: A—E and B—F are the same, different or mixed longer chain radicals containing 12-20 carbon atoms, with ring and/or branch chain stearic hindrance and able to wrap with the chains of polymer molecules or which contain functional groups able to cross link with polymer molecules.

2. The aluminate coupling agent as in claim 1, Wherein the number of radicals connected with aluminum atom is 4-6.

3. The aluminate coupling agent, as in claim 2 wherein 3 radicals are connected with aluminum by covalent bonding and 1-3 are non-chelating legands L, connecting with aluminum atoms by coordinate links.

4. The aluminate coupling agent as in claim 1, wherein L is selected from one of the group consisting of ketones, aldehydes, amines, alcohols, esters, and ethers.

5. The aluminate coupling agent as in claim 1, wherein the long chain radicals are aryl or aliphatic rings and secondary or tertiary carbon atoms.

6. The aluminate coupling agent as in claim 1 wherein the functional groups are those which can cross link with polymer molecules.

7. The aluminate coupling agent as in claim 6, Wherein the functional groups are a double bond, carboxylic ester link, ether link, sulfur link, isocyano group, azo-group or azido-group.

8. The aluminate coupling agent as in claim 1 comprising the lower condensed products and mixtures.

9. The aluminate coupling agent as in claim 8, wherein the lower condensed products and mixtures comprise the formula

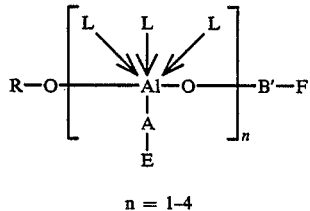

n = 1-4

Wherein n=1-4; RO is alkoxy or aryloxy containing 1-6 carbon atoms; L are ligands and their number is equal to 1, 2, or 3; A—E and $B^1$—F are longer chain radicals containing 12-20 or more carbon atoms, with ring and/or branch chain steric hindrance able to wrap with the chains of polymer molecules, or containing functional groups which can react with polymer molecules.

10. A process for synthesizing aluminate coupling agent of the structure:

wherein Al is the aluminum atom; RO is alkoxyl or aryloxy containing 1-6 carbon atoms; L are the same, different or mixed ligands having atoms with an isolated electron pair; A—E and B—F are the same, different or mixed longer chains radicals containing 12-20 carbon atoms, with ring and/or branch chain stearic hindrance and able to wrap with the chains of polymer molecules or which contain functional groups able to cross link with polymer molecules, which comprises reacting metallic aluminum with lower alcohols or phenols containing 1-6 carbon atoms, obtaining an intermediate trial koxyaluminum, reacting the intermediate with a compound selected from the group consisting of alcohols, phenols, carboxylic acids carboxylic esters, ethers and aldehydes having long chains with ring and/or branch chain steric hindrance and able to wrap with the chains of polymer molecules or contain functional groups which can cross-link with polymer molecules, and adding non-chelating ligand L which have an atom with an isolated pair of electrons.

11. The process as in claim 10, wherein the ring stearic hindrance is with reference to the hindrance of aryl or aliphatic rings with over 5 atoms.

12. The process as in claim 10, wherein the long chains are branch chains with a tertiary carbon atom.

13. The process, as in claim 10, wherein the alcohols, phenols, carboxylic acids esters, ethers and aldehydes have functional groups which can cross link with polymer molecules.

14. The process as in claim 13, wherein the functional groups are selected from the group consisting of double bonds carboxylic ester linkages, ether linkages sulfur linkages, azo-groups or azide-groups.

15. The process as in claim 14, wherein the ligands L are selected from the groups consisting of monoketones, aldehydes, amines esters, or ethers having atoms with an isolated electron pair.

16. The process as in claim 10, wherein if the alcohols, phenols, carboxylic acids, esters, ethers and aldehydes have the atom which contains an isolated electron pair in the position of 3-4 atoms from a hydroxy or carboxylic group, the number of ligand L may be reduced.

17. The aluminate coupling agent as in claim 5 wherein the long chain radicals are aryl or aliphatic rings with more than 5 carbon atoms and/or branch chains with tertiary carbon atoms.

18. The aluminate coupling agent consisting of an aluminate atom as the central atom in the molecule of the structure:

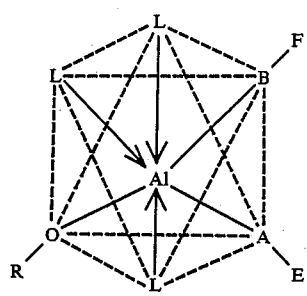

wherein Al is the aluminum atom, RO is alkoxy or aryloxy containing 1-6 carbon atoms, L are the same different or mixed ligands having atoms with an isolated election pair: A-E and B-F are the same, different or mixed longer chain radials containing 12-22 carbon atoms, with ring and/or branch chain steriric hindrance and able to wrap with the chains of polymer molecules or which contain functional groups able to cross link with polymer molecules.

* * * * *

UNITED STATES PATENT AND TRADEMARK OFFICE
CERTIFICATE OF CORRECTION

PATENT NO. : 4,816,594
DATED : MARCH 28, 1989
INVENTOR(S) : Wengong ZHANG, Wending CHEN, Tianan CHEN It is certified that error appears in the above-identified patent and that said Letters Patent is hereby corrected as shown below:

Title page:

Column 1 Item [75] which reads "Inventors: Zhang Wengong; Chen Wending; Chen Tianan" should read -- Wengong Zhang; Wending Chen; Tianan Chen--, Signed and Sealed this Twentieth Day of March, 1990

Attest:

JEFFREY M. SAMUELS

*Attesting Officer*   *Acting Commissioner of Patents and Trademarks*